(12) United States Patent
Mayo et al.

(10) Patent No.: US 12,150,690 B2
(45) Date of Patent: Nov. 26, 2024

(54) ELECTROSURGICAL TIP

(71) Applicant: Boston Scientific Scimed, Inc., Maple Grove, MN (US)

(72) Inventors: Joseph Mayo, Medford, MA (US); Matthew P. Jones, Shoreview, MN (US); Raymond Gessler, Roberts, WI (US); Asha D'Cunha, Hugo, MN (US); Serena Scott, Worcester, MA (US); Katrina Hansen, Shrewsbury, MA (US); Jeffery T. Lersch, Monticello, MN (US)

(73) Assignee: Boston Scentific Scimed, Inc., Maple Grove, MN (US)

( * ) Notice: Subject to any disclaimer, the term of this patent is extended or adjusted under 35 U.S.C. 154(b) by 312 days.

(21) Appl. No.: 16/941,913

(22) Filed: Jul. 29, 2020

(65) Prior Publication Data
US 2021/0030460 A1 Feb. 4, 2021

Related U.S. Application Data

(60) Provisional application No. 62/880,226, filed on Jul. 30, 2019.

(51) Int. Cl.
*A61B 18/08* (2006.01)
*A61B 18/00* (2006.01)
(Continued)

(52) U.S. Cl.
CPC ............ *A61B 18/082* (2013.01); *A61B 18/10* (2013.01); *C23C 14/14* (2013.01); *C23C 14/34* (2013.01);
(Continued)

(58) Field of Classification Search
CPC .................. A61B 18/082; A61B 18/10; A61B 2018/00077; A61B 2018/00148;
(Continued)

(56) References Cited

U.S. PATENT DOCUMENTS

| 4,532,924 A | 8/1985 | Auth et al. |
| 5,549,604 A | 8/1996 | Sutcu et al. |

(Continued)

FOREIGN PATENT DOCUMENTS

JP 2016527959 A 9/2016

OTHER PUBLICATIONS

International Search Report and Written Opinion for the International Patent Application No. PCT/US2020/044000, mailed Nov. 3, 2020, 13 pages.

*Primary Examiner* — Joseph A Stoklosa
*Assistant Examiner* — Annie L Shoulders
(74) *Attorney, Agent, or Firm* — Seager, Tufte & Wickhem, LLP

(57) ABSTRACT

The present disclosure relates generally to the field of medical devices. In particular, the present disclosure relates to an electrosurgical surgical tip that includes a conductive and low-profile cutting surface to provide high current density radiofrequency energy with minimal thermal damage to surrounding tissues. For example, an electrosurgical tip of the present disclosure may include a ring of conductive material sputter-coated around a distal opening of a non-conductive base component and a strip of conductive material sputter-coated along a longitudinal axis of the non-conductive base component.

14 Claims, 4 Drawing Sheets

(51) Int. Cl.
*A61B 18/10* (2006.01)
*C23C 14/14* (2006.01)
*C23C 14/34* (2006.01)
*C23C 28/02* (2006.01)

(52) U.S. Cl.
CPC .. *C23C 28/023* (2013.01); *A61B 2018/00077* (2013.01); *A61B 2018/00148* (2013.01); *A61B 2018/00601* (2013.01)

(58) Field of Classification Search
CPC .......... A61B 2018/00601; C23C 14/14; C23C 14/34; C23C 28/023
See application file for complete search history.

(56) References Cited

U.S. PATENT DOCUMENTS

| | | | |
|---|---|---|---|
| 5,925,039 A | 7/1999 | Landingham | |
| 6,213,995 B1* | 4/2001 | Steen | A61B 18/14 |
| | | | 604/527 |
| 8,870,864 B2 | 10/2014 | Davison et al. | |
| 8,962,062 B2 | 2/2015 | Podhajsky et al. | |
| 11,116,570 B2* | 9/2021 | Purdy | A61B 18/1492 |
| 11,309,140 B2* | 4/2022 | Lees | H01H 36/0006 |
| 2005/0222564 A1 | 10/2005 | Plaza et al. | |
| 2011/0160721 A1 | 6/2011 | Wang et al. | |
| 2013/0317351 A1* | 11/2013 | Case | A61B 90/37 |
| | | | 600/424 |
| 2014/0276748 A1* | 9/2014 | Ku | A61B 18/18 |
| | | | 606/33 |
| 2016/0274050 A1* | 9/2016 | Goodwin | C23C 14/3464 |
| 2016/0338768 A1* | 11/2016 | Beeckler | H01B 3/12 |
| 2016/0374755 A1* | 12/2016 | Mirigian | A61B 18/1492 |
| | | | 606/41 |
| 2018/0147007 A1 | 5/2018 | Purdy et al. | |
| 2018/0228538 A1* | 8/2018 | Roeder | A61B 18/1492 |
| 2018/0256200 A1 | 9/2018 | Benning et al. | |
| 2018/0289971 A1* | 10/2018 | Yeh | A61N 1/0558 |
| 2019/0099210 A1* | 4/2019 | Eggers | A61B 18/082 |
| 2021/0378738 A1* | 12/2021 | Hancock | A61B 18/1477 |
| 2022/0313462 A1 | 10/2022 | Gon | |

* cited by examiner

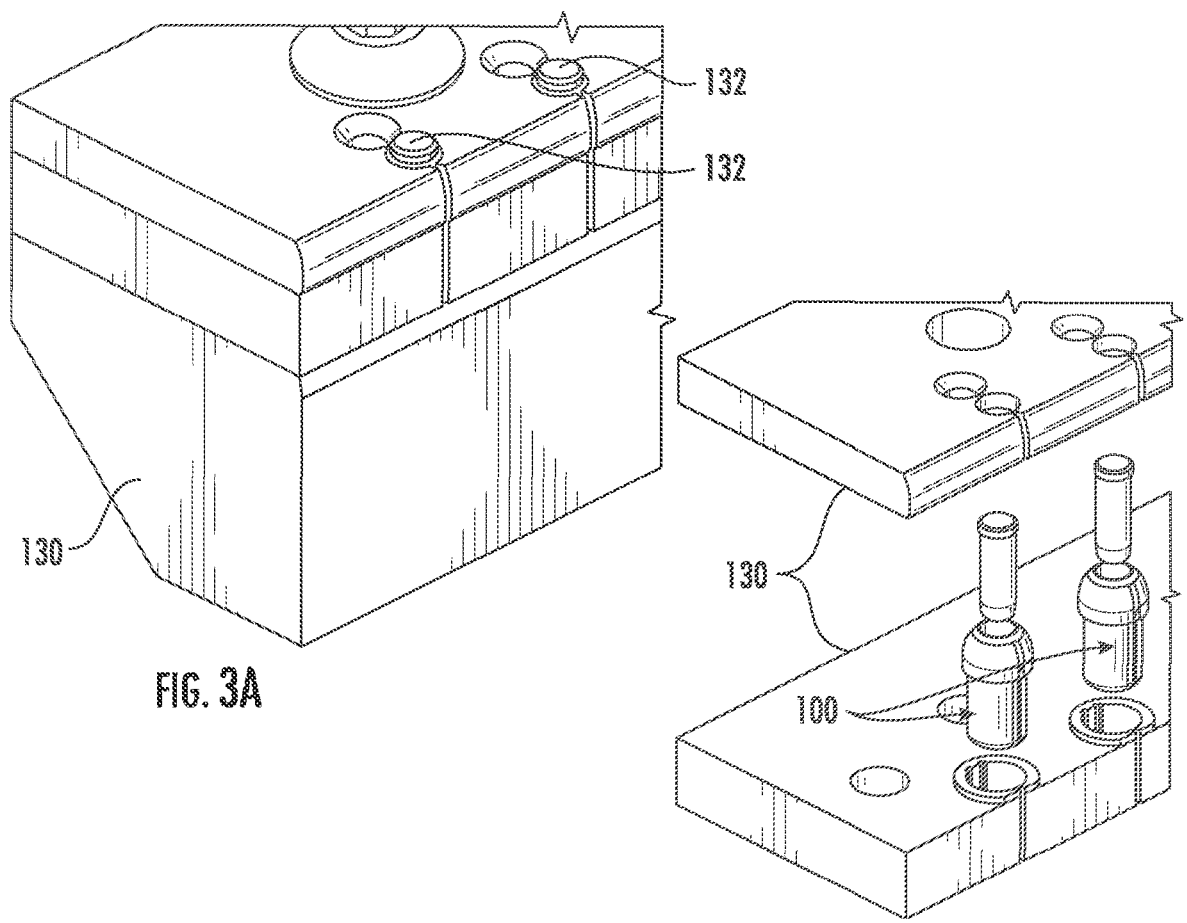
FIG. 3A
FIG. 3B
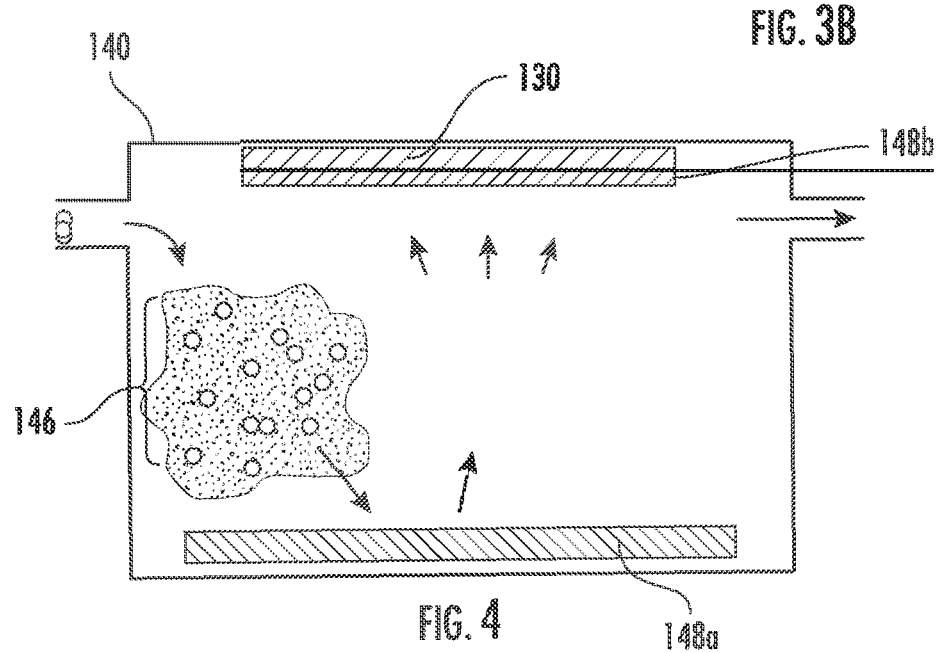
FIG. 4

ELECTROSURGICAL TIP

RELATED APPLICATIONS

This application claims the benefit of priority under 35 U.S.C. § 119 to U.S. Provisional Application No. 62/880,226, titled "Sputter-Coated Ceramic Electrosurgical Tip", filed on Jul. 30, 2019, the entirety of which is incorporated herein by reference.

FIELD

The present disclosure relates generally to the field of medical devices. In particular, the present disclosure relates to an electrosurgical surgical tip that includes a conductive and low-profile cutting surface to provide high current density radiofrequency energy with minimal thermal damage to surrounding tissues.

BACKGROUND

Many endoscopic ultrasound (EUS) guidance procedures involve creating a puncture tract (e.g., fistula) through the tissue layer(s) of a target anatomy using a tissue-penetrating needle, advancing a guidewire through the tissue-penetrating needle to position a distal end of the guidewire within the target anatomy and then advancing a medical device with a circular electrosurgical tip over the guidewire to dilate the puncture tract. To effectively dilate the tissue layer(s) with minimal thermal damage (e.g., charring, burning, coagulation, etc.), the electrosurgical tip must deliver radiofrequency energy with sufficient current density through a low surface area profile. Due to these design criteria, conventional electrosurgical tips tend to be expensive and difficult to manufacture.

It is with these considerations in mind that a variety of advantageous medical outcomes may be realized by the devices, systems and methods of the present disclosure.

SUMMARY

In one aspect, the present disclosure relates to a medical device comprising a non-conductive base component defining a longitudinal axis and a lumen therethrough. A conductive material may be disposed on an outer surface of the non-conductive base component around a distal opening of the lumen. A conductive material may be disposed on an outer surface of the non-conductive base component along the longitudinal axis. The conductive material disposed around the distal opening may include a first layer of conductive material bonded to the non-conductive base component. The conductive material disposed along the longitudinal axis may include a second layer of conductive material bonded to the non-conductive base component. The first and second layers of conductive material may be sputter-coated onto the non-conductive base component.

In the described and other embodiments, one or more of the first and second layers of conductive material may be sputter-coated onto the non-conductive base component. A channel may be formed within the outer surface of the non-conductive base component along the longitudinal axis. The second layer of conductive material may extend through the channel. The first and second layers of conductive material may include titanium. The conductive material disposed around the distal opening may further include a third layer of conductive material bonded to the first layer of conductive material and the conductive material disposed along the longitudinal axis may include a fourth layer of conductive material bonded to the second layer of conductive material. The third and fourth layers of conductive material may be sputter-coated onto the respective first and second layers of conductive material. The third and fourth layers of conductive material may include niobium. The conductive material disposed around the distal opening may further include a fifth layer of conductive material bonded to the third layer of conductive material. The conductive material disposed along the longitudinal axis may include a sixth layer of conductive material bonded to the fourth layer of conductive material. The fifth layer of conductive material may include gold. The sixth layer of conductive material may include a nickel-copper alloy. The fifth and sixth layers of conductive material may be sputter-coated onto the respective third a fourth layers of conductive material. The fifth layer of conductive material may be brazed to the third layer of conductive material. The sixth layer of conductive material may be sputter-coated onto the fourth layer of conductive material. A distal portion of a conductive wire may be soldered to the sixth layer of conductive material.

In another aspect, the present disclosure relates to a system comprising a non-conductive base component attached to a distal end of an electrosurgical sheath. The non-conductive base component may include a conductive material applied around a distal opening of the non-conductive base component and a strip of conductive material applied along a longitudinal axis of the non-conductive base component. An access cannula may be disposable within a lumen of the electrosurgical sheath and extendable through the non-conductive base component.

In the described and other embodiments, one or more of the conductive material and the strip of conductive material may be applied via sputter-coating. A channel may be formed within an outer surface of the non-conductive base component along the longitudinal axis. The strip of conductive material may extend through the channel. The channel may be disposed within a distal portion of the electrosurgical sheath. A distal portion of a conductive wire may be disposed within the channel. The distal portion of the conductive wire may be bonded to the channel using solder. The conductive wire may extend along the electrosurgical sheath and a proximal end of the conductive wire may be connectable to an electrosurgical generator. A guidewire may be extendable through a lumen of the access cannula.

In yet another aspect, the present disclosure relates to a medical device comprising a non-conductive base component defining a longitudinal axis and a lumen therethrough. A first layer of conductive material may be disposed around an outer surface of the non-conductive base component in a spiral pattern. A second layer of conductive material may be disposed around an outer surface of the non-conductive base component in a spiral pattern. The first and second layers of conductive material may be electrically insulated from each other.

In the described and other embodiments, the first and second layers of conductive material may be the same. The first and second layers of conductive material may be different. The first and second layers of conductive material may be sputter-coated to the non-conductive base component.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3A-3B provide perspective views of an electrosurgical tip housed within a fixture for physical vapor deposition, according to one embodiment of the present disclosure.

FIG. 4 provides a schematic illustration of a fixture (FIGS. 3A-3B) disposed within a physical-vapor deposition chamber, according to one embodiment of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to an electrosurgical surgical tip comprising one or more layers of conductive metal(s) coated onto a non-conductive ceramic base using physical vapor deposition (PVD), electroless plating, electrolytic plating or brazing, the disclosed devices and methods are not limited to medical devices or electrosurgical devices, but may include a variety of non-conductive devices coated with one or more layers of a variety of conductive materials.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In various embodiments, the present disclosure relates generally to a medical device (e.g., electrosurgical tip) comprising single or multiple layers of conductive material(s) precisely applied/deposited onto a non-conductive (e.g., ceramic) base in a controlled location and/or pattern and with a low surface area. The layer(s) of conductive material(s) may provide high current density radiofrequency (RF) energy and minimize or prevent collateral thermal damage to surrounding tissues. The components of the medical device local to the layer(s) of conductive material(s) may be electrically and thermally insulative to prevent harm to the patient and/or prevent thermal damage to the medical device itself.

Figure 1A:
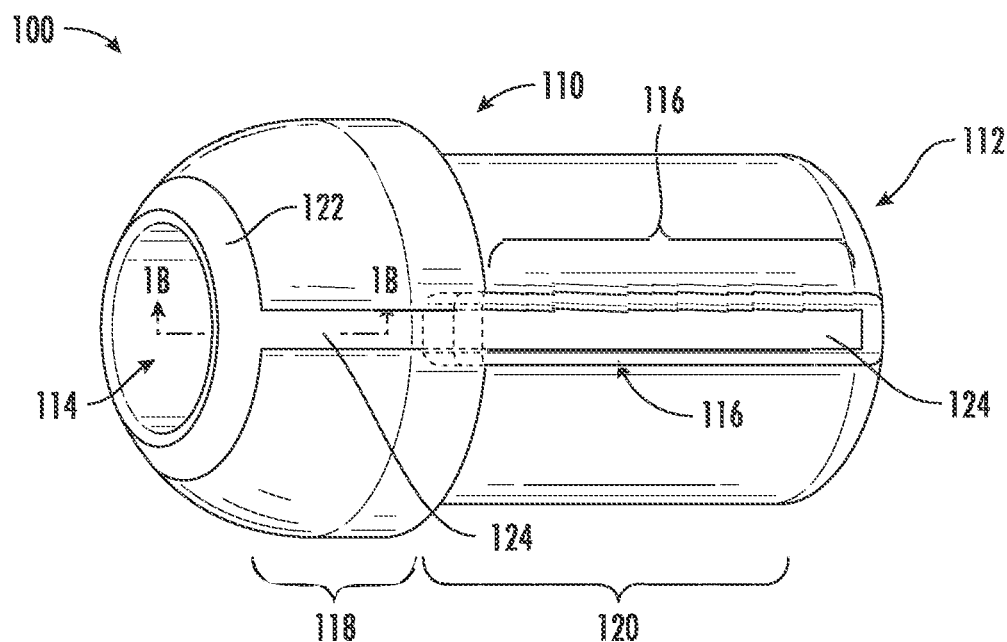
FIG. 1A provides a perspective view of an electrosurgical tip, according to one embodiment of the present disclosure.

Referring to FIG. 1A, in one embodiment, a medical device 100 (e.g., electrosurgical tip) of the present disclosure may include a non-conductive base component 110 comprising a conical or tapered distal portion 118 (e.g., an increasing taper or angled surface extending in a constant or varying distal to proximal direction) and a cylindrical proximal portion 120 (e.g., with a substantially constant outer dimension). A lumen 112 may extend along a longitudinal axis of the non-conductive base component 110. An outer dimension of the cylindrical proximal portion 120 may be less than a maximum outer dimension of the tapered distal portion 118. A groove or channel 116 may be formed within (e.g., extend along) an outer surface of the non-conductive base component 110 along the longitudinal axis of the proximal portion 120. In addition, the channel 116 may be formed within (e.g., extend along) a proximal end of the distal portion 118 of the non-conductive base component 110. In various embodiments, the non-conductive base component 110 may include a variety insulative materials, including, but not limited to ceramic, hard plastics and the like. A ring 122 (e.g., circular ring, trace, etc.) of conductive material may be disposed on an outer surface of the non-conductive base component 110 around a distal opening 114 of the lumen 112. A strip 124 (e.g., longitudinal strip, trace, etc.) of conductive material may be disposed on an outer surface of the distal and proximal portions 118, 120 along the longitudinal axis of the non-conductive base component 110. A distal end of the strip 124 may intersect, overlap or otherwise contact a portion of the ring 122 to provide a contiguous layer of conductive material (e.g., a single/unitary conductive layer) on/along the outer surfaces of the distal and proximal portions 118, 120 of the non-conductive base component 110. In various embodiments, a portion of the strip 124 of conductive material may be disposed within (e.g., extend through) the channel 116.

In one embodiment, the ring 122 of conductive material may include a first layer of conductive material bonded to the non-conductive base component 110 and the strip 124 of conductive material may include a second layer of conductive material bonded to the non-conductive base component 110. The first and second layers of conductive material may be the same or different materials. In various embodiments, the first and second layers of conductive material may include a metal (e.g., titanium) that provides the advantage of forming/creating a strong atomic bond (e.g., adhesion) with the non-conductive base component 110 (e.g., ceramic). In various embodiments, the first and/or second layers of conductive material may be applied or deposited to the non-conductive base component 110 using physical vapor deposition (e.g., sputter-coating, thermal evaporation, arc spraying, etc.), electroless plating, electrolytic plating or brazing, or other coating applications.

In one embodiment, the ring 122 of conductive material may include a third layer of conductive material bonded to the first layer of conductive material, and the strip 124 of conductive material may include a fourth layer of conductive material bonded to the second layer of conductive material. The third a fourth layers of conductive material may be the same or different materials (e.g., different from each other and/or different from the first and second layers of material). In various embodiments, the third and fourth layers of conductive material may include a metal (e.g., niobium) that provides the advantage of forming/creating a strong atomic bond (e.g., solderability) with the respective first and second layers of conductive material. In various embodiments, the third and fourth layers of conductive material may be applied or deposited to the non-conductive base component 110 using physical vapor deposition (e.g., sputter-coating, thermal evaporation, arc spraying, etc.), electroless plating, electrolytic plating or brazing or other coating applications.

Figure 1B:
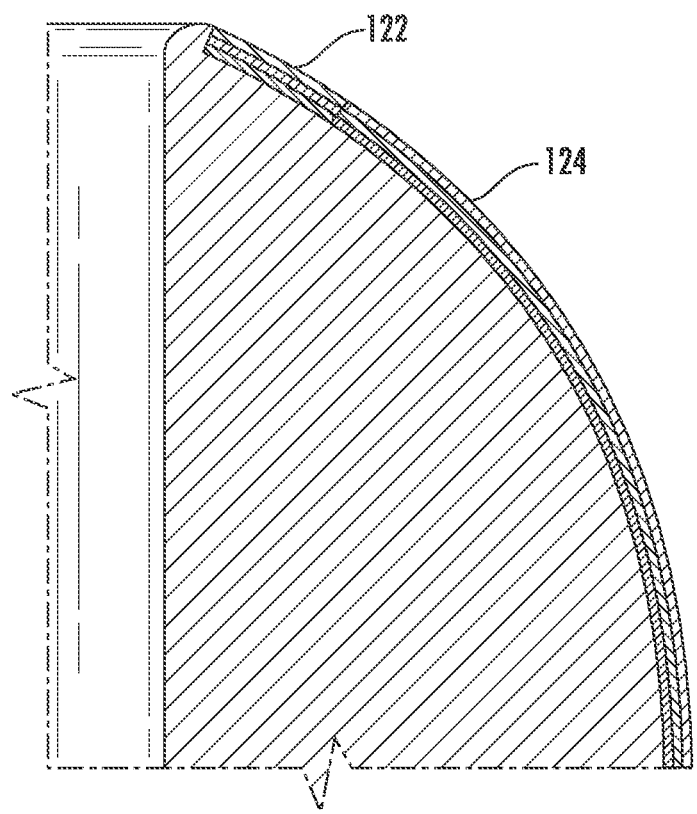
FIG. 1B provides a cross-sectional view of the various layers of conductive material, according to one embodiment of the present disclosure.
Figure 2:
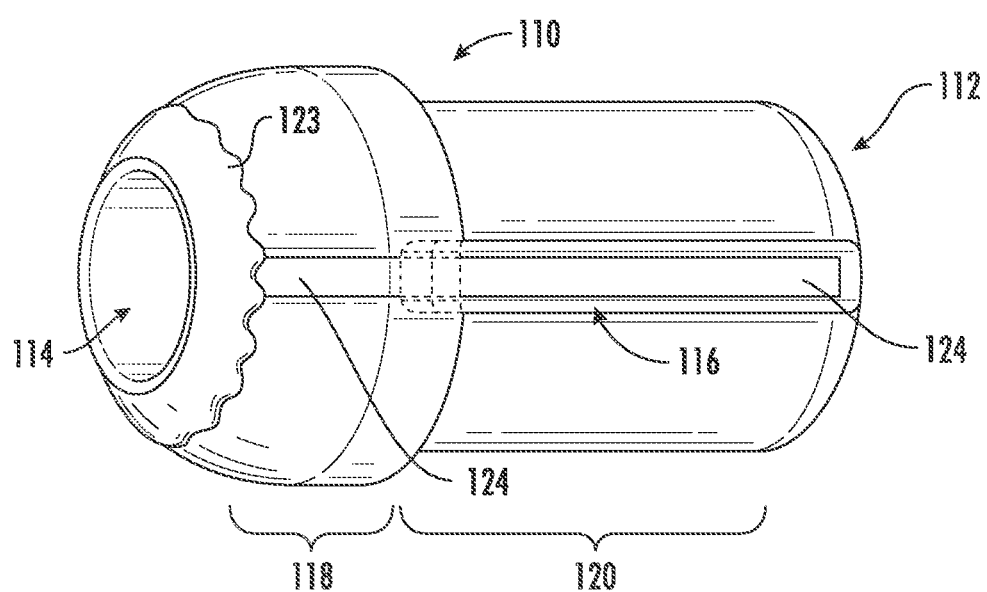
FIG. 2 provides a perspective view of an electrosurgical tip, according to one embodiment of the present disclosure.

In one embodiment, the ring 122 of conductive material may include a fifth layer of conductive material bonded to the third layer of conductive material, and the strip 124 of conductive material may include a sixth layer of conductive material bonded to the fourth layer of conductive material. The fifth and sixth layers of conductive material may be the same or different materials (e.g., different from each other and/or different from the first, second, third and fourth layers of material). In various embodiments, the fifth layer of conductive material may include a highly conductive metal (e.g., gold) that forms/creates a strong atomic bond with the third layer of conductive material. In various embodiments, the sixth layer of conductive material may include a conductive metal (e.g., nickel-copper alloy) that form/creates a strong atomic bond with the fourth layer of conductive material and which may form a strong atomic bond with a layer of solder (discussed below). In various embodiments, the fifth and sixth layers of conductive material may be applied or deposited to the non-conductive base component 110 using physical vapor deposition (e.g., sputter-coating, thermal evaporation, arc spraying, etc.), electroless plating, electrolytic plating or brazing or other coating applications. In one embodiment, the layers of conductive material comprising the ring 122 (e.g., first, third and fifth layers) and the layers of conductive material comprising the strip 124 (e.g., second, fourth and sixth layers) may intersect (e.g., overlap, touch, contact, etc.) each other in a variety of different patterns, layers and/or configurations to form a contiguous layer of conductive material (FIG. 1B). Alternatively, the fifth layer of conductive material may include a compatible filler material 123 (e.g., gold, silver, tin, etc.) brazed or welded (FIG. 2) to the non-conductive base component (e.g., rather than using physical vapor deposition), and the sixth layer of conductive material may be applied or deposited to the non-conductive base component 110 using physical vapor deposition (e.g., sputter-coating, thermal evaporation, arc spraying, etc.), electroless plating, electrolytic plating or brazing or other coating applications. In various embodiments, the brazed or welded layer of conductive material may provide a cutting surface with a geometry designed for a specific application (e.g., a raised, enlarged or thicker cutting surface, etc.).

In various embodiments, the ring 122 of conductive material may be the patient contacting portion (e.g., cutting surface) of the medical device 100 and the strip 124 of conductive material may be the non-patient contacting portion of the medical device. In one embodiment, a distal portion of a conductive wire (not shown) may be disposed within the groove 116 and attached to the sixth layer of conductive material by a layer of solder formed within the channel 116 on top of (e.g., over) the sixth layer of conductive material and the conductive wire disposed therebetween. A proximal end of the conductive wire may be electrically connected to an electrosurgical generator, as discussed below.

In various embodiments, an inner wall of the lumen 112 may not be coated with a conductive material to thermally and electrically insulate the lumen 112, and any medical devices extending therethrough (e.g., cannulas, guidewires, etc.), from the conductive ring 122 and/or strip 124. In various embodiments, the low profile/low surface area of the conductive ring 122 and strip 124 and the surrounding surfaces of the non-conductive base component 110 (e.g., distal portion 118, proximal portion 120, lumen 112) may conduct sufficient RF energy to efficiently cut through/penetrate various soft tissue walls (e.g., stomach, duodenum, gallbladder, pancreas, liver, etc.) with minimal collateral thermal damage to the surrounding tissues. The ring 122 may be disposed on a distalmost portion of the distal portion 118, such that tissue contacts the ring 122 first, and subjected to the RF energy for penetration through the tissue.

In various embodiments, the layer(s) of conductive material(s) may be applied/deposited on the non-conductive base component 110 using a line-of-sight PVD process that displaces metal atoms from a cathode using inert plasma atoms. Referring to FIGS. 3A-3B, in one embodiment, a non-conductive base component 110 of the present disclosure may be disposed within a fixture 130 which masks all outer surfaces of the non-conductive base component 110 except for the surfaces to which the ring 122 and strip 124 are to be applied. A plug or blank 132 may be disposed within the distal opening 114 of the non-conductive base component 110 to shield the lumen 112 from contact/coating with the atomized metals. Alternatively, the non-conductive base component 110 may be masked with a preformed tape, patternable coating, photoresist or other removable coating to delineate the ring 122 and strip 124.

Referring to FIG. 4, in one embodiment, the fixture 130 may be positioned within a sputter chamber 140 such that one side of the fixture 130 is directly opposite a metal target 148a (e.g., the conductive material to be sputtered). The sputter chamber 140 may serve as an anode, the metal target 148a may serve as a cathode and the inner surface of the sputter chamber 140 may serve as an electrode. An inert gas 146 (e.g., argon) may be pumped into the sputter chamber 140, energized to a plasma state and an electric field applied to bombard the cathode/metal target 148a. As the plasma atoms contact the metal target 148a, metal atoms may be displaced from the metal target 148a and directed towards the surface of the fixture 130. A thin layer (e.g., approximately 50 microns) of sputtered metal 148b may then form on the surface of the fixture 130, including the unmasked/exposed portion of the non-conductive base component 110 disposed therein. In various embodiments, the fixture 130 may be rotated within the sputter chamber 140 to expose the other unmasked surface of the non-conductive base component to the metal target 148a and the process repeated. In addition, the metal target 148a may be replaced with a different metal target to apply/deposit the various layers of metal to the respective portions (e.g., ring 122 and strip 124) of the non-conductive base component 110, as discussed above.

Figure 6:
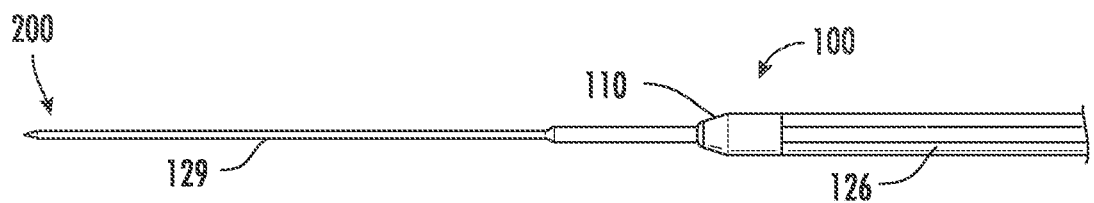
FIG. 6 provides a perspective view of an electrosurgical system, according to one embodiment of the present disclosure.

Referring to FIG. 6, in one embodiment, a system 200 of the present disclosure may include a non-conductive base component 110 of a medical device 100 attached to a distal end of a non-conductive electrosurgical sheath 126. In various embodiments, the proximal portion (not shown) of the non-conductive base component 110 may be received/disposed within a distal portion of the electrosurgical sheath 126 such that the channel 116 (not shown) and distal portion of the conductive wire (not shown) disposed therein are thermally and electrically insulated. The conductive wire may extend along the electrosurgical sheath 126 (e.g., embedded within a sidewall of the electrosurgical sheath) to connect a proximal end of the conductive wire to an electrosurgical generator. An access cannula 129 may be extendable through the lumen (not shown) of the non-conductive base component 110.

Figure 5A:
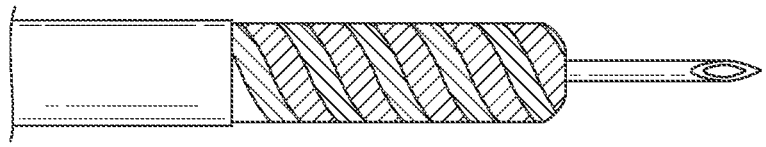
FIGS. 5A-5B provide perspective views of alternative electrosurgical tip configurations, according embodiments of the present disclosure.
Figure 5B:
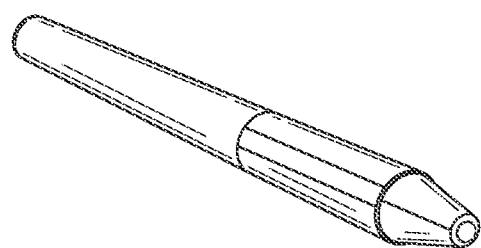

A variety of advantages may be realized by the devices, systems and methods of the present disclosure. For example, the disclosed layer(s) of conductive material(s) applied/deposited onto an outer surface of an electrosurgical device using PVD may allow for broader processing conditions at elevated temperature to provide finer surface features (e.g., lower surface area, lower profile, etc.), thereby reducing production costs, simplifying manufacturing, minimizing collateral thermal damage and maximizing patient safety. The disclosed PVD process may be applied to new medical devices and/or lower the cost of manufacturing or modifying existing medical devices. For example, the manual and expensive process involved in manufacturing a conventional electrosurgical tip, e.g., in which bi-polar traces of gold are printed in a spiral pattern around a non-conductive tip (Gold Probe™ Boston Scientific Corp., Marlborough Mass.; FIG. 5A) or a steel wire is formed around a ceramic tip (Hot Axios™ Boston Scientific Corp., Marlborough Mass.; FIG. 5B), may be modified to apply/deposit the bipolar or monopolar conductive layers using a PVD process. In various embodiments, for medical applications in which thicker conductive layers may be required, additional layer(s) of conductive material(s) may be applied to the PVD layer using electroless plating, electrolytic plating and/or brazing.

In various embodiments, the order in which the various layers of conductive materials outlined above (e.g., titanium, niobium, gold, nickel-copper alloy) may be applied/deposited to the non-conductive base component may be based on their respective properties of adhesion to the non-conductive base (e.g., ceramic), solderability (e.g., the ability to adhere/bond the highly conductive outer/top layer to the adhesive inner/bottom layer) and/or conductivity (e.g., of the outer/tissue contacting layer). It should be appreciated, however, that the present disclosure is in no way limited to these materials/metals, the number of layers of such materials and/or their order or pattern of deposition. A variety of conductive materials, including, by way of non-limiting example, titanium, niobium, gold, molybdenum, titanium nitride, tantalum, tungsten, platinum, palladium, iridium, tin, nickel, copper, vanadium, silver, zinc or other biocompatible metals, as well as alloys, oxides and nitrides of such materials may be applied/deposited on the disclosed medical device 100 in a variety of orders/layers, patterns and/or thicknesses.

In various additional embodiments, the number of layers of conductive material(s) applied to the non-conductive base component (e.g., the ring 122 and/or strip 124), is not limited to the first through sixth layers outlined above, but may include a single layer, two layers or any number of additional layers.

In various additional embodiments, the layers of conductive material comprising the ring 122 (e.g., first, third and fifth layers) and the layers of conductive material comprising the strip 124 (e.g., second, fourth and sixth layers) may intersect (e.g., overlap, touch, contact, etc.) each other in a variety of different patterns, layers and/or configurations to form a contiguous layer of conductive material. For example, a portion of the second layer may partially overlap a portion of the first layer of conductive material, a portion of the third layer of conductive material may partially overlap a portion of the second layer of conductive material, a portion of the fourth layer of conductive material may partially overlap a portion of the third layer of conductive material, a portion of the fifth layer of conductive material may partially overlap a portion of the fourth layer of conductive material and a portion of the sixth layer of conductive material may partially overlap a portion of the fifth layer of conductive material.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
a non-conductive base component defining a longitudinal axis and a lumen therethrough and having a channel formed within an outer surface along the longitudinal axis;
a conductive material disposed on an outer surface of the non-conductive base component around a distal opening of the lumen; and
a strip of conductive material disposed in the channel;
wherein the conductive material disposed around the distal opening includes a first layer of conductive material bonded to the non-conductive base component and the strip of conductive material disposed along the longitudinal axis includes a second layer of conductive material bonded to the non-conductive base component.

2. The medical device of claim 1, wherein one or more of the first and second layers of conductive material are sputter-coated onto the non-conductive base component.

3. The medical device of claim 1, wherein the first and second layers of conductive material include titanium.

4. The medical device of claim 1, wherein the conductive material disposed around the distal opening further includes a third layer of conductive material bonded to the first layer of conductive material and the strip of conductive material disposed along the longitudinal axis includes a fourth layer of conductive material bonded to the second layer of conductive material, and wherein the third and fourth layers of conductive material are sputter-coated onto the respective first and second layers of conductive material.

5. The medical device of claim 4, wherein the third and fourth layers of conductive material include niobium.

6. The medical device of claim 4, wherein the conductive material disposed around the distal opening further includes a fifth layer of conductive material bonded to the third layer of conductive material and the strip of conductive material disposed along the longitudinal axis includes a sixth layer of conductive material bonded to the fourth layer of conductive material.

7. The medical device of claim 6, wherein the fifth layer of conductive material includes gold and the sixth layer of conductive material includes a nickel-copper alloy.

8. The medical device of claim 6, wherein the fifth layer of conductive material is brazed to the third layer of conductive material and the sixth layer of conductive material is sputter-coated onto the fourth layer of conductive material.

9. The medical device of claim 6, further comprising a distal portion of a conductive wire soldered to the sixth layer of conductive material.

10. A system, comprising:
- a non-conductive base component having a channel formed within an outer surface along a longitudinal axis, the non-conductive base component attached to a distal end of an electrosurgical sheath, wherein the non-conductive base component includes a first layer of conductive material applied around a distal opening of the non-conductive base component and a strip of conductive material disposed in the channel; and
- an access cannula disposable within a lumen of the electrosurgical sheath and extendable through the lumen and out the distal opening of the non-conductive base component,
- wherein the strip of conductive material disposed along the longitudinal axis includes a second layer of conductive material bonded to the non-conductive base component.

11. The system of claim 10, wherein one or more of the conductive material and the strip of conductive material are applied via sputter-coating.

12. The system of claim 10, further comprising a distal portion of a conductive wire disposed within the channel.

13. The system of claim 12, wherein the conductive wire extends along the electrosurgical sheath and a proximal end of the conductive wire is connectable to an electrosurgical generator.

14. The system of claim 10, wherein a guidewire is extendable through a lumen of the access cannula.

* * * * *